United States Patent [19]

Maurer et al.

[11] 4,254,113

[45] Mar. 3, 1981

[54] COMBATING ARTHROPODS WITH O-ALKYL-O-(2-CYCLOPROPYL-6-METHYL-PYRIMIDIN-4-YL)-THIONOPHOSPHONIC ACID ESTERS

[75] Inventors: Fritz Maurer; Rolf Schröder, both of Wuppertal; Ingeborg Hammann, Cologne; Wolfgang Behrenz, Overath-Steinenbrueck; Wilhelm Stendel, Wuppertal, all of Fed. Rep. of Germany

[73] Assignee: Bayer Aktiengesellschaft, Leverkusen, Fed. Rep. of Germany

[21] Appl. No.: 51,282

[22] Filed: Jun. 22, 1979

[30] Foreign Application Priority Data

Jul. 15, 1978 [DE] Fed. Rep. of Germany ....... 2831165

[51] Int. Cl.³ .................. A01N 57/24; C07F 9/65
[52] U.S. Cl. ..................................... 424/200; 544/243
[58] Field of Search .................... 544/243; 424/200

[56] References Cited

U.S. PATENT DOCUMENTS

| 3,216,894 | 11/1965 | Lorenz et al. | 424/200 |
| 3,932,631 | 1/1976 | Cotterrell | 424/200 |
| 4,012,506 | 3/1977 | Balke et al. | 424/200 |
| 4,115,542 | 9/1978 | Maurer et al. | 424/200 |
| 4,155,999 | 5/1979 | Maurer et al. | 424/200 |

*Primary Examiner*—Donald G. Daus
*Assistant Examiner*—Diana G. Rivers
*Attorney, Agent, or Firm*—Sprung, Felfe, Horn, Lynch & Kramer

[57] ABSTRACT

O-Alkyl-O-(2-cyclopropyl-6-methyl-pyrimidin-4-yl)-thionophosphonic acid esters of the formula

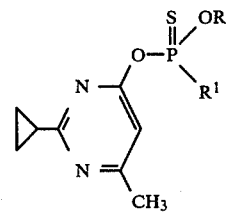

in which
$R_1$ is alkyl, and
$R^1$ is alkyl or phenyl, which possess arthropodicidal properties.

9 Claims, No Drawings

COMBATING ARTHROPODS WITH O-ALKYL-O-(2-CYCLOPROPYL-6-METHYL-PYRIMIDIN-4-YL)-THIONOPHOSPHONIC ACID ESTERS

The present invention relates to and has for its objects the provision of particular new O-alkyl-O-(2-cyclopropyl-6-methylpyrimidin-4-yl)-thionophosphonic acid esters which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known that O-alkyl-O-(2,6-dialkyl-pyrimidin-4-yl)-thiono-phosphonic acid esters, for example O-methyl-O-(2,6-dimethyl-pyrimidin-4-yl)-methane-thionophosphonic acid ester, O-ethyl-O-(2,6-dimethyl-pyrimidin-4-yl)-methane-thionophosphonic acid ester and O-methyl-O-(2,6-dimethyl-pyrimidin-4-yl)-ethane-thionophosphonic acid ester, have an insecticidal and acaricidal action (see U.S. Pat. No. 3,216,894). However, the action of these compounds is not always satisfactory, especially when low amounts and concentrations are used.

The present invention now provides, as new compounds, the 2-cyclopropyl-pyrimidin-4-yl-thionophosphonic acid esters of the general formula

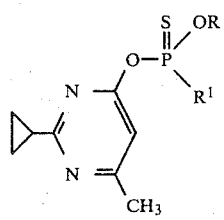

in which
R represents alkyl and
$R^1$ represents alkyl or phenyl.

The new active compounds are distinguished by their high activity in combating pests, in particular by a high insecticidal and acaricidal activity.

Preferably, in formula (I), R represents straight-chain or branched alkyl with 1 to 5 (especially with 1 to 3) carbon atoms, and $R^1$ represents straight-chain or branched alkyl with 1 to 5 (especially with 1 to 3) carbon atoms, or phenyl.

Surprisingly, the 2-cyclopropyl-pyrimidin-4-yl-thionophosphonic acid esters according to the invention exhibit a better activity in combating pests, in particular a better insecticidal and acaricidal action, then the corresponding compounds of analogous structure and the same type of action which are known from the state of the art. The products according to the present invention thus represent a valuable enrichment of the art.

The invention also provides a process for the preparation of a 2-cyclopropyl-pyrimidin-4-yl-thionophosphonic acid ester of the formula (I) in which a thionophosphonic acid ester halide of the general formula

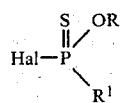

in which
R and $R^1$ have the meanings stated above and
Hal represents chlorine or bromine,
is reacted with 2-cyclopropyl-6-methyl-4-hydroxy-pyrimidine, of the formula

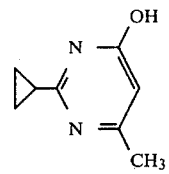

if appropriate in the presence of an acid acceptor and if appropriate in the presence of a diluent.

If, for example, O-iso-propyl-n-propane-thionophosphonic acid ester-chloride and 2-cyclopropyl-6-methyl-4-hydroxy-pyrimidine are used as starting substances, the reaction can be outlined by the equation which follows:

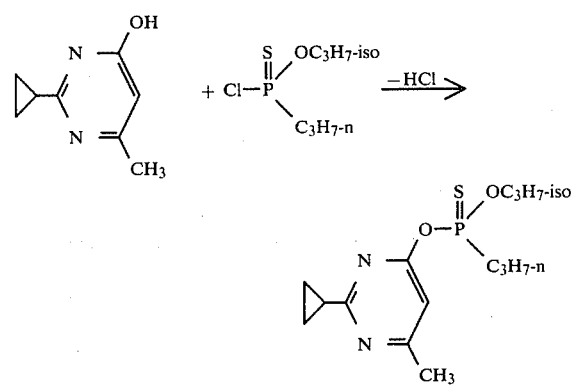

The formula (II) provides a definition of the thionophosphonic acid ester halides to be used as starting substances. Preferably, in this formula, R and $R^1$ have the meanings stated to be preferred in connection with formula (I) and Hal represents chlorine.

The starting compounds of the formula (II) are known. Examples which may be mentioned are: O-methyl-, O-ethyl-, O-n-propyl- and O-iso-propyl-methane-thionophosphonic acid ester-chloride, O-methyl-, O-ethyl-, O-n-propyl- and O-isopropyl-ethane-thionophosphonic acid ester-chloride, O-methyl-, O-ethyl-, O-n-propyl- and O-iso-propyl-propane-thionophosphonic acid ester-chloride and O-methyl-, O-ethyl-, O-n-propyl- and O-iso-propyl-phenyl-thionophosphonic acid ester-chloride.

The 2-cyclopropyl-6-methyl-4-hydroxy-pyrimidine to be employed as the second reactant is known (see U.S. Pat. No. 4,012,506).

The process of the preparation of the 2-cyclopropyl-pyrimidin-4-yl-thionophosphonic acid esters according to the invention is preferably carried out using a suitable solvent or diluent. Possible solvents and diluents are virtually any of the inert organic solvents, especially aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

Any of the customary acid-binding agents can be used as the acid acceptors. Alkali metal carbonates and alcoholates, such as sodium carbonate and potassium carbonate and sodium methylate or ethylate and potassium methylate or ethylate, and furthermore aliphatic, aromatic or heterocyclic amines, for example triethylamine, trimethylamine, dimethylaniline, dimethylbenzylamine and pyridine, have proved particularly suitable.

The reaction temperature can be varied within a substantial range. In general, the reaction is carried out at from 0° to 100° C., preferably at from 20° to 80° C. The process according to the invention is generally carried out under normal pressure.

The starting materials are usually employed in equimolar amounts for carrying out the process according to the invention. An excess of one or other of the reactants brings no considerable advantages. The reaction is in general carried out in a suitable diluent in the presence of an acid acceptor, and the reaction mixture is stirred at the required temperature for several hours. Thereafter, an organic solvent, for example toluene, is added and the organic phase is worked up in the customary manner by washing and drying and distilling off the solvent.

The new compounds are obtained in the form of oils, some of which cannot be distilled without decomposition, but which can be freed from the last volatile constituents by so-called "incipient distillation", that is to say by prolonged heating to moderately elevated temperatures under reduced pressure, and can be purified in this manner. The refractive index is used for their characterization.

The 2-cyclopropyl-pyrimidin-4-yl-thionophosphonic acid esters according to the invention are distinguished as agents for combating pests, in particular by an outstanding insecticidal and acaricidal activity against plant pests, pests harmful to health and pests of stored products. They have a good action against sucking and biting insects and mites.

For this reason, the compounds according to the invention can successfully be employed as agents for combating pests in the protection of plants and in the hygiene field, the field of protection of stored products and the veterinary field.

The active compounds are well tolerated by plants, have a favorable level of toxicity to warm-blooded animals, and can be used for combating arthropod pests, especially insects and acarids which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca grgaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cinciticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogas-* ter, Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Lactrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application of said animals of a compound according to the present invention, in admixture with a diluent or carrier.

The preparation of the novel compounds is shown in the following illustrative example:

EXAMPLE 1

(a) The 2-cyclopropyl-4-hydroxy-6-methylpyrimidine to be employed as a starting material could be prepared, for example, as follows:

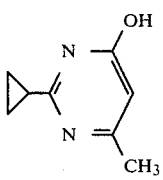

(III)

78.3 g (0.65 mol) of cyclopropylamidine hydrochloride and then 76.4 g (0.65 mol) of acetoacetic acid methyl ester were added to a solution of 70 g (1.3 mol) of sodium methylate in 400 ml of methanol at room temperature. The mixture was stirred at room temperature for 18 hours, the solvent was then distilled off in vacuo and the residue was dissolved in 400 ml of water. The solution was adjusted to pH 4 by adding concentrated hydrochloric acid and, after cooling to 5°–10° C., the product which had precipitated was filtered off. 75 g (77% of theory) of 2-cyclopropyl-4-hydroxy-6-methylpyrimidine were obtained in this manner in the form of a colorless powder with the melting point 187° C.

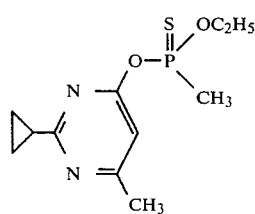

(1)

A mixture of 15 g (0.1 mol) of 2-cyclopropyl-4-hydroxy-6-methyl-pyrimidine, 20.7 g (0.15 mol) of potassium carbonate, 15.9 g (0.1 mol) of O-ethyl-methanethionophosphonic acid ester-chloride and 300 ml of acetonitrile was stirred at 50° C. for 4 hours. The mixture was then cooled to room temperature and, after adding 400 ml of toluene, was extracted by shaking twice with 300 ml of water each time. The organic phase was separated off, dried over sodium sulphate and freed from the solvent in vacuo and the residue was subjected to incipient distillation. 21.8 g (81% of theory) of O-ethyl-O-(2-cyclopropyl-6-methyl-pyrimidin-4-yl)-methanethionophosphonic acid ester were thus obtained in the form of a yellow oil with the refractive index $n_D^{22}$: 1.5367.

The following compounds of the general formula

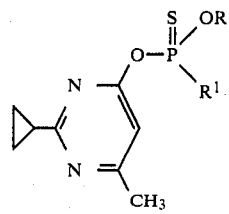

(I)

could be prepared analogously:

TABLE

| Compound No. | R | $R^1$ | Yield (% of theory) | Refractive index: |
|---|---|---|---|---|
| 2 | $C_2H_5$ | phenyl | 80 | $n_D^{22}$:1.5761 |
| 3 | $C_2H_5$ | $C_2H_5$ | 87 | $n_D^{22}$:1.5372 |
| 4 | $C_3H_7$-iso | $CH_3$ | 77 | $n_D^{22}$:1.5276 |
| 5 | $C_3H_7$-n | $C_2H_5$ | | |
| 6 | $CH_3$ | $CH_3$ | | |
| 7 | $CH_3$ | $C_2H_5$ | 86 | $n_D^{20}$:1.5404 |
| 8 | $CH_3$ | phenyl | | |

The pesticidal activity of the compounds of this invention is illustrated by the following examples wherein the compounds according to the present invention are each identified by the number (given in brackets) from Example 1:

EXAMPLE 2

Plutella test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were treated by being dipped into the preparation of active compound of the desired concentration and were infested with caterpillars of the diamond-back moth (Plutella maculipennis), as long as the leaves were still moist.

After the specified periods of time, the degree of destruction was determined as a percentage: 100% meant that all of the caterpillars were killed whereas 0% meant that none of the caterpillars were killed.

In this test, for example, the following compounds showed a superior activity compared to the prior art: (1), (2), (3) and (4).

EXAMPLE 3

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Bean plants (Phaseolus vulgaris) which were heavily infested with the two-spotted spider mite (Tetranychus

*urticae*) in all stages of development were treated by being dipped into the preparation of the active compound of the desired concentration.

After the specified periods of time, the degree of destruction was determined as a percentage: 100% meant that all of the spider mites were killed whereas 0% meant that none of the spider mites were killed.

In this test, for example, the following compounds showed a superior activity compared to the prior art: (2), (3) and (4).

EXAMPLE 4

Mosquito larvae test
Test insects: Aedes aegypti larvae (4th stage)
Solvent: 99 parts by weight of acetone
Emulsifier: 1 part by weight of benzylhydroxydiphenyl polyglycol ether To produce a suitable preparation, the active compound was dissolved, at a rate of 2 g per liter, in the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage. 100% meant that all of the larvae were killed. 0% meant that none of the larvae were killed.

In this test, for example, the following compounds showed a superior action compared to the prior art: (1), (2), (3) and (4).

EXAMPLE 5

Test with parasitic adult cattle ticks (*Boophilus microplus* res.)
Solvent: Alkylaryl polyglycol ether To produce a suitable preparation of active compound, the active substance in question was mixed with the stated solvent in the ratio of 1:2 and the concentrate thus obtained was diluted with water to the desired concentration.

10 adult cattle ticks (*B. microplus* res.) were dipped for 1 minute into the active compound preparation to be tested. After transfer into plastic beakers and storage in a climatically controlled chamber, the degree of destruction was determined.

In this test, for example, the following compounds showed a superior action compared to the prior art: (1) and (3).

EXAMPLE 6

Test with parasitic fly larvae
Emulsifier: 80 parts by weight of alkylaryl polyglycol ether To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction was determined.

In this test, for example, the following compounds showed a superior action compared to the prior art: (1) and (3).

It will be appreciated that the instant specification and examples are set forth by way of illustration and not limitation, and that various modifications and changes may be made without departing from the spirit and scope of the present invention.

We claim:

1. An O-alkyl-O-(2-cyclopropyl-6-methyl-pyrimidin-4-yl)-thionophosphonic acid ester of the formula

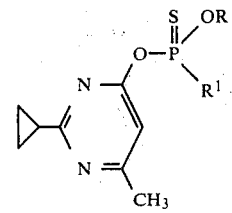

in which
R is alkyl with 1 to 5 carbon atoms, and
$R^1$ is alkyl with 1 to 5 carbon atoms or phenyl.

2. A compound according to claim 1, wherein such compound is O-ethyl-O-(2-cyclopropyl-6-methyl-pyrimidin-4-yl)-methanethionophosphonic acid ester of the formula

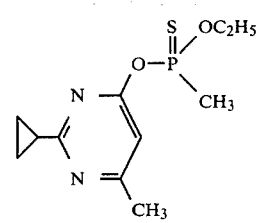

3. A compound according to claim 1, wherein such compound is O-ethyl-O-(2-cyclopropyl-6-methyl-pyrimidin-4-yl)-phenylthionophosphoric acid ester of the formula

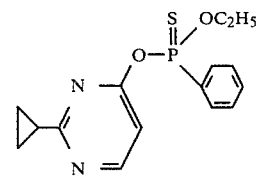

4. A compound according to claim 1, wherein such compound is O-ethyl-O-(2-cyclopropyl-6-methyl-pyrimidin-4-yl)-ethanethionophosphonic acid ester of the formula

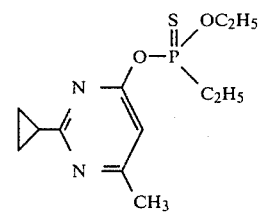

5. A compound according to claim 1, wherein such compound is O-isopropyl-O-(2-cyclopropyl-6-methylpyrimidin-4-yl)-methanethionophosphonic acid ester of the formula

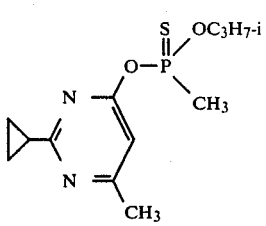

6. A compound according to claim 1, wherein such compound is O-methyl-O-(2-cyclopropyl-6-methyl-pyrimidin-4-yl)-ethanethionophosphonic acid ester of the formula

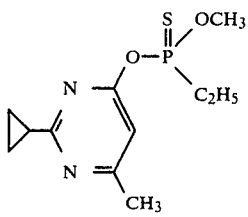

7. An arthropodicidal composition containing as active ingredient an arthropodicidally effective amount of a compound according to claim 1 in admixture with a diluent.

8. A method of combating arthropods which comprises applying to the arthropods, or to a habitat thereof, an arthropodicidally effective amount of a compound according to claim 1.

9. The method according to claim 8, wherein the compound is
O-ethyl-O-(2-cyclopropyl-6-methyl-pyrimidin-4-yl)-methanethionophosphonic acid ester,
O-ethyl-O-(2-yclopropyl-6-methyl-pyrimidin-4-yl)-phenylthionophosphoric acid ester,
O-ethyl-O-(2-cyclopropyl-6-methyl-pyrimidin-4-yl)-ethanethionophosphonic acid ester,
O-isopropyl-O-(2-cyclopropyl-6methyl-pyrimidin-4-yl)-methanethionophosphonic acid ester, or
O-methyl-O-(2-cyclopropyl-6-methyl-pyrimidin-4-yl)-ethanethionophosphonic acid ester,
and it is applied to domesticated animals.

* * * * *

UNITED STATES PATENT AND TRADEMARK OFFICE
CERTIFICATE OF CORRECTION

PATENT NO. : 4,254,113

DATED : Mar. 3, 1981

INVENTOR(S) : Fritz Maurer et al

It is certified that error appears in the above-identified patent and that said Letters Patent are hereby corrected as shown below:

Column 10, line 51  Delete "N=" and insert --N=\CH$_3$ --.

Signed and Sealed this

Eleventh Day of August 1981

[SEAL]

Attest:

GERALD J. MOSSINGHOFF

Attesting Officer

Commissioner of Patents and Trademarks